United States Patent
Vidal et al.

(10) Patent No.: US 6,238,440 B1
(45) Date of Patent: May 29, 2001

(54) KERATIN FIBRE DYE COMPOSITIONS CONTAINING PYRROLO-AZOLE COMPOUNDS, USE THEREOF AS COUPLERS, AND DYEING METHOD

(75) Inventors: Laurent Vidal, Paris; Gérard Malle, Villiers sur Morin, both of (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 09/142,951

(22) PCT Filed: Mar. 24, 1997

(86) PCT No.: PCT/FR97/00517

§ 371 Date: Mar. 25, 1999

§ 102(e) Date: Mar. 25, 1999

(87) PCT Pub. No.: WO97/35554

PCT Pub. Date: Oct. 2, 1997

(30) Foreign Application Priority Data

Mar. 22, 1996 (FR) .................................................. 96 03627

(51) Int. Cl.[7] ...................................................... A61K 7/13
(52) U.S. Cl. ............................ 8/409; 8/423; 8/573; 8/574
(58) Field of Search ................................. 8/409, 423, 573, 8/574

(56) References Cited

U.S. PATENT DOCUMENTS

| | | | |
|---|---|---|---|
| 3,061,432 | 10/1962 | Menzel et al. | 430/376 |
| 3,227,554 | 1/1966 | Barr et al. | 430/382 |
| 3,419,391 | 12/1968 | Young | 430/387 |
| 3,725,067 | 4/1973 | Bailey et al. | 430/476 |
| 3,820,948 | 6/1974 | Berth | 8/409 |
| 3,926,631 | 12/1975 | Arai et al. | 430/226 |
| 4,128,425 | 12/1978 | Greenwald | 430/440 |
| 4,293,543 | 10/1981 | Cotte et al. | 8/405 |
| 4,500,630 | 2/1985 | Sato et al. | 430/386 |
| 5,256,526 | 10/1993 | Suzuki et al. | 430/384 |
| 5,441,863 | 8/1995 | Tang et al. | 430/558 |
| 5,457,210 | 10/1995 | Kim et al. | 548/262.4 |

FOREIGN PATENT DOCUMENTS

| | | |
|---|---|---|
| 2 160 317 | 6/1973 | (DE) . |
| 2 359 999 | 6/1975 | (DE) . |
| 3 731 395 | 4/1989 | (DE) . |
| 3 843 892 | 6/1990 | (DE) . |
| 4 009 097 | 9/1991 | (DE) . |
| 4 133 957 | 4/1993 | (DE) . |
| 0 030 680 | 6/1981 | (EP) . |
| 0 119 860 | 9/1984 | (EP) . |
| 0 285 274 | 10/1988 | (EP) . |
| 0 304 001 | 2/1989 | (EP) . |
| 0 309 652 | 4/1989 | (EP) . |
| 0 320 764 | 6/1989 | (EP) . |
| 0 456 226 | 11/1991 | (EP) . |
| 0 488 248 | 6/1992 | (EP) . |
| 0 488 909 | 6/1992 | (EP) . |
| 0 518 238 | 12/1992 | (EP) . |
| 0 547 864 | 6/1993 | (EP) . |
| 0 557 851 | 9/1993 | (EP) . |
| 0 578 248 | 1/1994 | (EP) . |
| 0 591 103 | 4/1994 | (EP) . |
| 1 564 999 | 4/1969 | (FR) . |
| 2 075 583 | 10/1971 | (FR) . |
| 2 466 492 | 4/1981 | (FR) . |
| 2 486 913 | 3/1987 | (FR) . |
| 1 026 978 | 3/1963 | (GB) . |
| 1 153 196 | 6/1966 | (GB) . |
| 1 458 377 | 9/1974 | (GB) . |
| 58-42045 | 3/1983 | (JP) . |
| 59-99437 | 6/1984 | (JP) . |

(List continued on next page.)

OTHER PUBLICATIONS

R. Stollé, "Ueber die Ueberführung der secundären Säure-hydrazide in Derivate des Furodiazols, Pyrrodiazols und Thiodiazols", Chemischen Gesellschaft, pp. 797–798, 1899, No month available.

(List continued on next page.)

Primary Examiner—Caroline D. Liott
(74) Attorney, Agent, or Firm—Finnegan, Henderson, Farabow, Garrett & Dunner, L.L.P.

(57) ABSTRACT

The present invention relates to a composition for the dyeing of keratinous fibres, especially human hair, which comprises, in a medium appropriate for dyeing:

as coupler, at least one compound corresponding to one of the formulae:

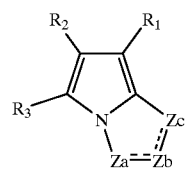

(I)

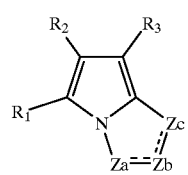

(II)

in which $R_1$ is especially hydrogen, halogen, aryloxy, alkoxy, acyloxy, arylthio, alkylthio, heteroarylthio, heteroaryloxy, etc;

$R_2$ and $R_3$ are independent and are especially hydrogen, halogen, alkyl, aryl, alkylthio, arylthio, benzylthio, etc;

$Z_a$, $Z_b$ and $Z_c$ are independent and are a nitrogen atom or a carbon atom carrying a radical $R_4$, $R_5$, $R_6$ or $R_7$;

$R_4$, $R_6$ and $R_7$ are identical or different and are especially hydrogen, alkyl, aryl, a heterocycle, a halogen, etc; and $R_5$ is especially hydrogen, halogen, acyl, acyloxy or carbamoyl, etc;

and at least one oxidation base.

60 Claims, No Drawings

FOREIGN PATENT DOCUMENTS

| | | |
|---|---|---|
| 59-162548 | 9/1984 | (JP) . |
| 59-171956 | 9/1984 | (JP) . |
| 60-33552 | 2/1985 | (JP) . |
| 60-43659 | 3/1985 | (JP) . |
| 60-172982 | 9/1985 | (JP) . |
| 60-190779 | 9/1985 | (JP) . |
| 62-279337 | 12/1987 | (JP) . |
| 63-169571 | 7/1988 | (JP) . |
| 62 36011 | 8/1994 | (JP) . |
| 7-36159 | 2/1995 | (JP) . |
| 7-84348 | 3/1995 | (JP) . |
| 7-92632 | 4/1995 | (JP) . |
| WO 92/04349 | 3/1992 | (WO) . |
| WO 92/04883 | 4/1992 | (WO) . |
| WO 94/04130 | 3/1994 | (WO) . |
| WO 94-89970 | 4/1994 | (WO) . |
| WO 94/08959 | 4/1994 | (WO) . |
| WO 94/08969 | 4/1994 | (WO) . |

OTHER PUBLICATIONS

Hans Beyer et al., "Über die Pyrazolbidung aus α–Chlor–acetessigester und Thiocarbohydazid", Chemische Berichte, pp. 2550–2555, 1956, No month available.

H. Wilde et al., Synthese von 4H–Pyrazolo[1,5–α]benzimidazolen, Journal Für Praktische Chemie, pp. 829–836, 1984, No month available.

Lidia Wyzgowska et al., "O Reakcjach Trikarboetoksymetanu VIII", Acta Poloniae Pharmaceutica, pp. 83–88, 1982, No month available.

E. Hannig et al., "Zur Kenntnis des 4–aminierten Phenylbutazons", Die Pharmazie, pp. 231, 1980, No month available.

Giuliana Cardillo et al., "Su due constituenti minori della Kamala", Gazetta Chimica Italiana, pp. 725–734, 1965, No month available.

Thomas Kauffmann et al., Synthese von Amidrazonon aus Nitrilen und Natriumhydrazid, pp. 3436–3443, 1964, No month available.

von Helmut Dorn et al., "Synthese und Methylierung von 1H–Pyrazolo[3,4–b]pyrazinen, einer neuen Klasse von Purin–Antagonisten", Annalen der Chemie, pp. 118–123, 1968, No month available.

von Helmut Dorn et al., "Über die elektrophile Substitution von 3(5)–Amino–pyrazol", Annalen der Chemie, pp. 141–146, 1967, No month available.

Mohamed Helmi Elnagdi et al., "Studies on 3,5–pyrazolidinediones. IV. Addition of 4–Arylazo–3,5–pyrazolidinediones to Ethyl Acrylate", Bulletin of Them Chemical Society of Japan, vol. 46, pp. 1830–1833, 1973, No month available.

Günther Ege et al., "A Simple Synthesis of 3(5)–Aminopyrazole", Angew. Chem. internat. Edit, vol. 13, No. 3, pp. 206–207, 1974, No month available.

Kazumasa Takahashi et al., "Syntheses of 3(5)–Substitued–4–(N–methylanilino)–5(3)–aminopyrazoles by Reaction of β–Hydroxy–α–cyano–enamines with Hydrazines", Journal of Synthetic Organic Chemistry, No. 8, pp. 794–796, 1985, No month available.

Chiara B. Vincentini et al., "Pyrazolo[3,4–d][1,2,3]Triazole–1–carboxamides and 5–Alkylaminopyrazolo[3,4–d]oxazoles: Synthesis and Evaluation of the in Vitro Antifungal Activity", II Farmaco, vo. 47, No. 7, 8, pp. 1021–1034, 1992, No month available.

Edward C. Taylor et al., "Reaction of Malononitrile with Substituted Hydrazines: New Routes to 4–Aminopyrazolo[3,4–d]pyrimidines", Journal of the merican Chemical Society, vol. 81, No. 10, pp. 2456–2464, 1959, No month available.

C.B. Vincentini et al., "A New Fused Heterocyclic System: 6H–Pyrazolo[3,4–c][1,2,5]thiadizine 2,2–Dioxide", Journal of Heterocyclic Chemistry, vol. 26, No. 3, pp. 797–803, 1989, No month available.

E.J. Browne et al., "Triazoles, Part VII. Syntheses of Substituted 1,2,4–Triazoles", Journal of The Chemical Society, pp. 5149–5152, 1962, No month available.

Philip Magnus et al., "Synthesis of helical Poly–β–pyrroles. Multiple Atropisomerism Resulting in Helical Enantiomorphic Conformations", Journal of the American Chemical Society, vol. 112, No. 6, pp. 2465–2468, 1990, No month available.

Paul Carter et al., "Studies on the Synthesis of the Antitumor Agent CC–1065. Synthesis of PDE I and PDE II, Inhibitors of Cyclic Adenosine–3',5'–monophosphate Phosphodiesterase Using the 3,3'–Bipyrrole Strategy", Journal of the American Chemical Society, vol. 109, No. 9, pp. 2711–2717, 1987, No month available.

H. Koopman, "Investigations on Herbicides IV, The synthesis of 2,6–dichlorobenzonitrile", Recueil, vol. 80, No. 9–10, pp. 1075–1083, 1961, No month available.

Joseph Bailey, "Synthesis of 1H–Pyrazolo[3,2–c]–s–Triazoles and Derived Azamethine Dyes", Journal of the Chemical Society, pp. 2047–2052, 1977, No month available.

Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyramidines", Jounral f. prakt. chemie, Band 320, heft 4, pp. 533–538, 1978, No month available.

KERATIN FIBRE DYE COMPOSITIONS CONTAINING PYRROLO-AZOLE COMPOUNDS, USE THEREOF AS COUPLERS, AND DYEING METHOD

The invention relates to a composition for the dyeing of keratinous fibres, especially human hair, which comprises at least one pyrrolo-azole compound as coupler and at least one oxidation base.

It is known to dye keratinous fibres, and especially human hair, with dyeing compositions comprising oxidation dye precursors, especially ortho- or para-phenylenediamines, ortho- or para-aminophenols and heterocyclic compounds, which are referred to generally as oxidation bases. The oxidation dye precursors, or oxidation bases, are colourless or slightly coloured compounds which, when combined with oxidizing products, are able to give rise to coloured compounds and dyes by a process of oxidative condensation.

It is also known that the shades obtained with these oxidation bases can be varied by combining them with couplers or coloration modifiers, the latter being selected in particular from aromatic meta-diamines, meta-aminophenols, meta-diphenols and certain heterocyclic compounds, such as indole compounds.

The variety of molecules employed as oxidation bases and couplers makes it possible to obtain a wide range of colours.

The "permanent" coloration obtained by means of these oxidation dyes is required, moreover, to meet a certain number of requirements. Hence it must have no toxicological drawbacks, must allow shades of the desired intensity to be obtained, and must have good resistance to external agents (light, inclement weather, washing, permanent-waving, perspiration and friction).

The dyes must also allow white hair to be covered and, finally, they must be as unselective as possible; in other words, they must allow the smallest possible differences in coloration to be produced over the entire length of a single keratinous fibre, which may in fact be sensitized (i.e. damaged) differently between its tip and its root.

The Applicant has now discovered that it is possible to obtain new, powerful dyes, of low selectivity and particularly high resistance, which are capable of giving rise to intense colorations in various shades, using pyrrolo-azole compounds as couplers in the presence of an oxidation base.

It is this discovery which forms the basis of the present invention.

The invention provides a composition for the dyeing of keratinous fibres and, in particular, of human keratinous fibres, such as hair, which is characterized in that it comprises, in a medium appropriate for dyeing:

as coupler, at least one pyrrolo-azole compound corresponding to one of the following formulae (I) and (II), or one of its addition salts with an acid:

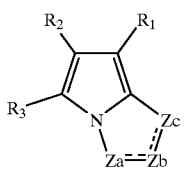

(I)

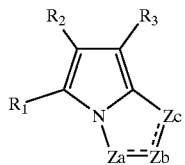

(II)

in which:

$R_1$ is: a hydrogen atom; a halogen atom such as bromine, chlorine or fluorine; an acetylamido group; an alkoxy radical (such as, for example: methoxy, ethoxy, propyloxy, benzyloxy, methoxyethoxy, phenoxyethoxy, 2-cyanoethoxy, phenethyloxy, p-chlorobenzyloxy or methoxyethylcarbamoylmethoxy); an aryloxy radical (such as, for example: phenoxy, 4-methoxyphenoxy, 4-nitrophenoxy, 4-cyanophenoxy, 4-methanesulphonamidophenoxy, 4-methanesulphonylphenoxy, 3-methylphenoxy or 1-naphthyloxy); an acyloxy radical (such as, for example: acetoxy, propanoyloxy, benzoyloxy, 2,4-dichlorobenzoyloxy, ethoxyalkyloxy, pyruvyloyloxy, cinnamoyloxy or myristoyloxy); an arylthio radical (such as, for example: phenylthio, 4-carboxyphenylthio, 2-ethoxy-5-tert-butylphenylthio, 2-carboxyphenylthio or 4-methanesulphonylphenylthio); an alkylthio radical (such as, for example: methylthio, ethylthio, propylthio, butylthio, 2-cyanoethylthio, benzylthio, phenethylthio, 2-(diethylamino)ethylthio, ethoxyethylthio or phenoxyethylthio); a heteroarylthio radical (such as, for example: 5-phenyl-2,3,4,5-tetrazolylthio, 2-benzothiazolylthio); a heteroaryloxy radical (such as, for example: 5-phenyl-2,3,4,5-tetrazolyloxy or 2-benzothiazolyloxy); a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical; an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridinyl radical; an alkylamido; an arylamido; a radical $NR^{III}R^{IV}$ where $R^{III}$ and $R^{IV}$ are identical or different and are a $C_1$–$C_4$ alkyl; a hydroxyalkyl; a carboxyl; or an alkoxycarboxyl radical;

$R_2$ and $R_3$ are independently of one another a hydrogen atom; a halogen atom (such as bromine, chlorine or fluorine); a linear or branched $C_1$–$C_5$ alkyl radical which is optionally substituted by one or two halogen, hydroxyl, alkoxy, aryloxy, amino, alkylamino, acyl or acylamino radicals; a $C_1$–$C_4$ alkoxy radical; a $C_1$–$C_4$ alkylthio radical; an arylthio radical; a benzylthio radical; an acyl radical (such as acetyl, 3-phenylpropanoyl, benzoyl or 4-dodecyloxybenzoyl); an acylamino radical; an acyloxy radical (such as acetoxy); a carbamoyl radical (such as carbamoyl, N-ethylcarbamoyl, N-phenylcarbamoyl, N,N-dibutylcarbamoyl or N-(2-dodecyloxyethyl)carbamoyl); a phenyl radical which is optionally substituted by one or two halogen, nitro, sulphonyl, $C_1$–$C_4$ alkoxy, $C_1$–$C_4$ alkyl, $C_1$–$C_3$ trifluoroalkyl, amino or alkylamino groups; an alkoxycarbonyl radical (such as methoxycarbonyl, ethoxycarbonyl, isopropyloxycarbonyl, tert-butyloxycarbonyl, isobutyloxycarbonyl, butylcarbamoylethoxycarbonyl or perfluorohexylethoxycarbonyl); an aryloxycarbonyl radical (such as phenoxycarbonyl or 2,5-diamylphenoxycarbonyl); a cyano radical; a nitro radical; a dialkylphosphono radical (such as dimethylphosphono); a diarylphosphono radical (such as diphenylphosphono); a dialkoxyphospholyl radical (such as dimethoxyphospholyl); a dialkylphosphinyl radical (such as dimethylphosphinyl); a diarylphosphinyl radical (such as diphenylphosphinyl); an alkylsulphinyl radical (such as 3-phenoxypropylsulphinyl); an arylsulphinyl radical (such as 3-phenoxypropylsulphinyl); an arylsulphonyl radical (such as benzenesulphonyl or toluenesulphonyl); an alkylsulphonyl radical (methanesulphonyl, octanesulphonyl); a sulphonyloxy radical (such as methanesulphonyloxy or toluenesulphonyloxy); an acylthio radical (such as acetylthio or benzoylthio); a sulphamoyl radical (such as N-ethylsulphamoyl, N,N-diisopropylsulphamoyl or N,N-diethylsulphamoyl); a thiocyanate radical; or a thiocarbonyl radical (such as methylthiocarbonyl or phenylthiocarbonyl);

$Z_a$, $Z_b$ and $Z_c$ are independently of one another a nitrogen atom or a carbon atom carrying a radical $R_4$, $R_5$, $R_6$ or $R_7$;

$R_4$, $R_6$ and $R_7$ are identical or different and are a hydrogen atom; a linear or branched $C_1$–$C_{20}$ alkyl radical which is optionally substituted by 1 or 2 radicals R selected from the group consisting of halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl and acyl; an aryl radical (such as phenyl or naphthyl) which is optionally substituted by 1 or 2 radicals R as defined above; a 5- or 6-membered heterocycle having at least one nitrogen, oxygen or sulphur atom (such as pyridyl, quinolyl, pyrrolyl, morpholyl, furyl, tetrahydrofuryl, pyrazolyl, triazolyl, tetrazolyl, thiazolyl, oxazolyl, imidazolyl or thiadiazolyl) and being optionally substituted by 1 or 2 radicals R as defined above;

when $R_4$, $R_6$ and $R_7$ are an alkyl radical, an aryl radical or a 5- or 6-membered heterocycle (defined above), the radical or heterocycle may be attached to the carbon atom of the ring system via an oxygen, nitrogen or sulphur atom (in this case, $R_4$, $R_6$ and $R_7$ become $XR_4$, $XR_6$ or $XR_7$ where X=O, NH, S);

$R_4$, $R_6$ and $R_7$ may also be a halogen atom (such as bromine, chlorine or fluorine); an acyl radical; a sulphonyl radical; a sulphinyl radical; a phosphonyl radical; a carbamoyl radical; a sulphamoyl radical; a cyano radical; a siloxy radical; an amino radical; an acylamino radical; an acyloxy radical; a carbamoyloxy radical; a sulphonamide radical; an imide radical; a ureido radical; a sulphamoylamino radical; an alkoxycarbonylamino radical; an aryloxycarbonylamino radical; an alkoxycarbonyl radical; an aryloxycarbonyl radical; or a carboxyl radical;

$R_5$ is hydrogen; halogen; an acyl radical; an acyloxy radical; a carbamoyl radical; an alkoxycarbonyl radical; a cyano radical; a nitro radical; a dialkylphosphono radical; a diarylphosphono radical; a dialkoxyphospholyl radical; a dialkylphosphinyl radical; a diarylphosphinyl radical; an alkylsulphinyl radical; an arylsulphinyl radical; an alkylsulphonyl radical; an arylsulphonyl radical; a sulphonyloxy radical; an acylthio radical; a sulphamoyl radical; a thiocyanate radical; a thiocarbonyl radical; a haloaryloxy radical (such as pentafluorophenyloxy); a haloalkylamino (such as N,N-di(trifluoromethylamino)); a haloalkylthio (such as difluoromethylthio); an aryl which is unsubstituted or substituted by electron-withdrawing groups (for example Cl, $NO_2$, F); or a heterocycle (such as 2-benzoxazolyl, 2-benzothiazolyl, pyrazolyl, 5-chloro-1-tetrazolyl or 1-pyrrolyl);

and at least one oxidation base.

Among the radicals $R_1$ of formulae (I) and (II) preference is given to radicals selected from the group consisting of:

a hydrogen atom; a $C_1$–$C_4$ alkoxy; phenoxy; phenoxy substituted by a halogen atom, a $C_1$–$C_4$ alkyl, a carboxyl or a trifluoromethyl group; an acyloxy radical; benzyloxy; $C_1$–$C_4$ alkylthio; phenylthio; phenylthio substituted by a halogen atom, a $C_1$–$C_4$ alkyl, a carboxyl or a trifluoromethyl group; a $C_1$–$C_4$ alkylamido; phenylamido; a radical $NR^{III}R^{IV}$ where $R^{II}$ and $R^{IV}$ are identical or different and are a $C_1$–$C_4$ alkyl, a $C_1$–$C_4$ hydroxyalkyl; a carboxyl or a $C_1$–$C_4$ alkoxycarboxyl radical.

Among the radicals $R_1$ of the formulae (I) and (II) defined above, particular preference is given to radicals selected from the group consisting of:

hydrogen; chlorine or bromine; methoxy or ethoxy; phenyloxy; 4-methylphenyloxy; acyloxy; benzyloxy; methylthio or ethylthio; phenylthio; 4-methylphenylthio; 2-tert-butylphenylthio; acetamido; phenylacetamido; dimethylamino; diethylamino; ethylmethylamino; and (β-hydroxyethyl)methylamino.

In addition, very particular preference is given to radicals $R_1$ selected from the group consisting of: hydrogen; chlorine; ethoxy; phenoxy; benzyloxy; acyloxy; acetamido; and dimethylamino.

Among the radicals $R_2$ and $R_3$ of the formulae (I) and (II), preference is given to radicals selected from the group consisting of:

acyl; acyloxy; carbamoyl; alkoxycarbonyl; aryloxycarbonyl; cyano; nitro; alkylsulphinyl; arylsulphinyl; alkylsulphonyl; arylsulphonyl; sulphamoyl; haloalkyl; $C_1$–$C_4$ alkyl; and hydrogen.

Among the radicals $R_2$ and $R_3$ of the formulae (I) and (II) defined above, particular preference is given to radicals selected from the group consisting of:

acyl (such as acetyl, ethylcarbonyl or phenylcarbonyl); alkoxycarbonyl (such as methoxy- or ethoxycarbonyl); nitro; cyano; arylsulphonyl (such as phenylsulphonyl); carbamoyl (such as carbamoyl or N-ethylcarbamoyl); haloalkyl (such as trifluoromethyl); hydrogen; and $C_1$–$C_4$ alkyl (such as methyl or ethyl).

In addition, very particular preference is given to radicals $R_2$ selected from the group consisting of: cyano; hydrogen; methyl; and phenyl, and to the radicals $R_3$ selected from the group consisting of: alkoxycarbonyl, such as methoxycarbonyl or ethoxycarbonyl; aryloxycarbonyl; hydrogen; methyl; and cyano.

Among the radicals $R_4$, $R_6$ and $R_7$ of the formulae (I) and (II), preference is given to radicals selected from the group consisting of:

a linear or branched $C_1$–$C_4$ alkyl radical; aryl, such as phenyl; phenyl substituted by a halogen, a methoxy radical, a nitro group, a cyano group, a trifluoromethyl group or an amino group; cyano; nitro; acylamino; arylamino; alkylthio, such as methylthio or ethylthio; arylthio, such as phenylthio; carbamoyl, such as carbamoyl or N-ethylcarbamoyl; sulphonyl, such as methylsulphonyl; alkoxycarbonyl, such as methoxycarbonyl or ethyloxycarbonyl; aryloxycarbonyl, such as phenoxycarbonyl; acyl, such as acetyl or ethylcarbonyl; and hydrogen.

Additionally, very particular preference is given to the radicals $R_4$, $R_6$ and $R_7$ of the formulae (I) and (II) selected from the group consisting of:

hydrogen; linear or branched $C_1$–$C_4$ alkyl (such as methyl, ethyl or isopropyl); aryl, such as phenyl; and phenyl substituted by a halogen, a methoxy radical, a nitro group, a cyano group, a trifluoromethyl group or an amino group.

Among the radicals $R_5$ of the formulae (I) and (II) defined above, particular preference is given to radicals selected from the group consisting of:

acyl (such as acetyl, benzoyl or ethylcarbonyl); alkoxycarbonyl (such as methoxy- or ethoxycarbonyl or isopropoxycarbonyl); aryloxycarbonyl such as phenoxycarbonyl; nitro; cyano; arylsulphonyl (such as phenylsulphonyl); haloalkyl (such as trifluoromethyl); and a hydrogen.

Additionally, very particular preference is given to the radicals $R_5$ selected from the group consisting of: cyano; alkoxycarbonyl (such as methoxy- or ethoxycarbonyl); aryloxycarbonyl, such as phenoxycarbonyl; haloalkyl (such as trifluoromethyl); and a hydrogen.

Among the preferred compounds of the invention corresponding to the formula (I), mention may be made of those selected from the group consisting of:

(i) the pyrrolo[1,2-b]-1,2,4-triazoles of formula:

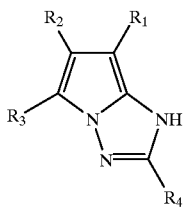

(Ia)

(ii) the pyrrolo[2,1-c]-1,2,4-triazoles of formula:

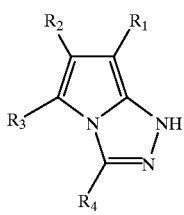

(Ib)

in which $R_1$, $R_2$, $R_3$ and $R_4$ are as defined above.

As examples of compounds of formula (Ia), particular mention may be made of those for which:

$R_1$ is hydrogen or chlorine;

$R_2$ and $R_3$ are, respectively: cyano and cyano; ethyloxycarbonyl and cyano; trifluoromethyl and cyano; phenylsulphonyl and cyano; trifluoromethyl and ethyloxycarbonyl; ethyloxycarbonyl and ethyloxycarbonyl; methyloxycarbonyl and methyloxycarbonyl; hydrogen and hydrogen; or hydrogen and methyl; and $R_4$ is methyl, ethyl, isopropyl, phenyl or hydrogen.

Among the compounds of formula (Ia) above, very particular mention may be made of:
3,4-dicyano-8-methylpyrrolo[1,2-b]-1,2,4-triazole,
3,4-dicyano-8-phenylpyrrolo[1,2-b]-1,2,4-triazole,
3,4-dicyano-8-tert-butylpyrrolo[1,2-b]-1,2,4-triazole,
5-chloro-3,4-dicyano-8-methylpyrrolo[1,2-b]-1,2,4-triazole,
and their addition salts with an acid.

As examples of compounds of formula (Ib) particular mention may be made of those for which:

$R_1$ is hydrogen or chlorine;

$R_2$ and $R_3$ are simultaneously cyano or hydrogen; and $R_4$ is methyl, ethyl, isopropyl, phenyl or hydrogen.

Among the compounds of formula (Ib) above, very particular mention may be made of:
5,6-dicyano-3-methylpyrrolo[2,1-c]-1,2,4-triazole,
7-chloro-5,6-dicyano-3-methylpyrrolo[2,1-c]-1,2,4-triazole,
and their addition salts with an acid.

Among the preferred compounds of the invention corresponding to formula (II), mention may be made of those selected from the group consisting of:

a) the pyrrolo[1,2-b]-1,2,4-triazoles of formula:

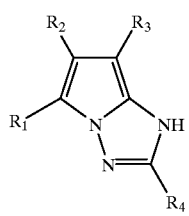

(IIa)

b) the pyrrolo[2,1-c]-1,2,4-triazoles of formula:

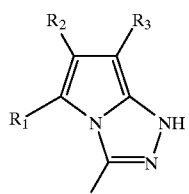

(IIb)

c) the pyrrolo[1,2-c]imidazoles of formula:

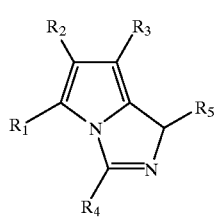

(IIc)

d) the pyrrolo[1,2-e]tetrazoles of formula:

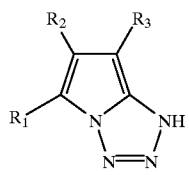

(IId)

e) the pyrrolo[1,2-a]pyrroles of formula:

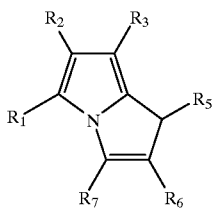

(IIe)

f) the pyrrolo[1,2-a]imidazoles of formula:

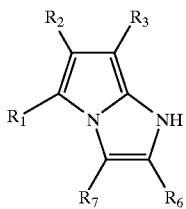

(IIf)

g) the pyrrolo[1,2-c]-1,2,3-triazoles of formula:

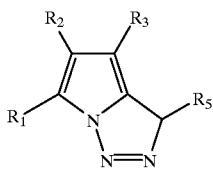

(IIg)

in which $R_4$, $R_5$, $R_6$ and $R_7$ are as defined above.

As examples of compounds of formula (IIa), mention may be made in particular of those for which:
$R_1$ is hydrogen or chlorine;
$R_2$ and $R_3$ are, respectively: methoxycarbonyl and cyano; ethyloxycarbonyl and cyano; cyano and methoxycarbonyl or ethoxycarbonyl; cyano and trifluoromethyl; cyano and phenylsulphonyl; methyloxycarbonyl and methyloxycarbonyl; hydrogen and hydrogen; hydrogen and methyl; trifluoromethyl and cyano or trifluoromethyl and methyloxycarbonyl; carboxyl and cyano; cyano and cyano; ethyloxycarbonyl and ethyloxycarbonyl; phenyl and cyano; methyl and hydrogen; and
$R_4$ is methyl, ethyl, isopropyl, phenyl or hydrogen.

Among the compounds of formula (IIa) above, very particular mention may be made of:
5-cyano-4-ethoxycarbonyl-8-methylpyrrolo[1,2-b]-1,2,4-triazole,
5-cyano-4-carboxy-8-methylpyrrolo[1,2-b]-1,2,4-triazole,
4,5-dicyano-8-methylpyrrolo[1,2-b]-1,2,4-triazole,
5-cyano-8-methyl-4-phenylpyrrolo[1,2-b]-1,2,4-triazole,
4,8-dimethylpyrrolo[1,2-b]-1,2,4-triazole,
4,5-di(ethyloxycarbonyl)-8-methylpyrrolo[1,2-b]-1,2,4-triazole,
3-chloro-5-cyano-4-ethoxycarbonyl-8-methylpyrrolo-[1,2-b]-1,2,4-triazole,
5-cyano-4-ethoxycarbonyl-8-phenylpyrrolo[1,2-b]-1,2,4-triazole,
5-cyano-4-carboxy-8-phenylpyrrolo[1,2-b]-1,2,4-triazole,
4,5-dicyano-8-phenylpyrrolo[1,2-b]-1,2,4-triazole,
4,5-di(ethyloxycarbonyl)-8-phenylpyrrolo[1,2-b]-1,2,4-triazole,
3-chloro-5-cyano-4-ethoxycarbonyl-8-phenylpyrrolo-[1,2-b]-1,2,4-triazole,
4-cyano-5-carboxy-8-(2-nitro-5-hydroxyphenyl)pyrrolo-[1,2-b]-1,2,4-triazole, and their addition salts with an acid.

As examples of compounds of formula (IIb), mention may be made in particular of those for which:
$R_1$ is hydrogen or chlorine;
$R_2$ and $R_3$ are, respectively: cyano and methoxycarbonyl; methoxycarbonyl and cyano; methoxycarbonyl and methoxycarbonyl; hydrogen and hydrogen or hydrogen and methyl; cyano and cyano; ethyloxycarbonyl and ethyloxycarbonyl; phenyl and cyano; tert-butyl and cyano; and
$R_4$ is methyl, ethyl, isopropyl, phenyl or hydrogen.

Among the compounds of formula (IIb) above, very particular mention may be made of:
6,7-dicyano-3-methylpyrrolo[2,1-c]-1,2,4-triazole,
5-chloro-6,7-dicyano-3-methylpyrrolo[2,1-c]-1,2,4-triazole,
6,7-di(ethyloxycarbonyl)-3-methylpyrrolo[2,1-c]-1,2,4-triazole,
7-cyano-3-methyl-6-phenylpyrrolo[2,1-c]-1,2,4-triazole,
7-cyano-3-methyl-6-tert-butylpyrrolo[2,1-c]-1,2,4-triazole,
and their addition salts with an acid.

As examples of compounds of formula (IIc), particular mention may be made of those for which:
$R_1$ is acetamido, chlorine or hydrogen;
$R_2$ and $R_3$ are, respectively: methoxycarbonyl and cyano; or cyano and cyano;
$R_4$ is hydrogen; and
$R_5$ is cyano.

Among the compounds of the formula (IIc) above, very particular mention may be made of:
6,8-dicyano-5-ethoxycarbonylpyrrolo[1,2-c]imidazole,
4-chloro-6,8-dicyano-5-ethoxycarbonylpyrrolo[1,2-c]-imidazole,
and their addition salts with an acid.

As examples of compounds of formula (IId), particular mention may be made of those for which:
$R_1$ is hydrogen or chlorine; and
$R_2$ and $R_3$ are, respectively: cyano and methoxycarbonyl; cyano and cyano; methoxycarbonyl and cyano; methoxycarbonyl and methoxycarbonyl; hydrogen and hydrogen or hydrogen and methyl.

Among the compounds of formula (IId) above, very particular mention may be made of:
6,7-dicyanopyrrolo[1,2-e]tetrazole,
6-cyano-7-ethoxycarbonylpyrrolo[1,2-e]tetrazole,
5-chloro-6,7-dicyanopyrrolo[1,2-e]tetrazole,
and their addition salts with an acid.

As examples of compounds of formula (IIe), particular mention may be made of those for which:
$R_1$ is hydrogen or chlorine;
$R_2$ and $R_3$ are, respectively: cyano and methoxycarbonyl;
$R_5$ is trifluoromethyl;
$R_6$ is phenyl or methyl; and
$R_7$ is methyl.

As examples of compounds of formula (IIf), particular mention may be made of those for which:
$R_1$ is hydrogen or chlorine; and
$R_2$, $R_3$, $R_6$ and $R_7$ are, respectively:
methoxycarbonyl/cyano/cyano/phenyl;
cyano/methoxycarbonyl/cyano/phenyl;
cyano/methoxycarbonyl/methoxycarbonyl/phenyl;
hydrogen/hydrogen/hydrogen/hydrogen; or
hydrogen/hydrogen/methyl/methyl.

Among the compounds of formula (IIf) above, very particular mention may be made of:

2,3,7-tricyano-6-methylpyrrolo[1,2-a]imidazole,
2,3,7-tricyano-6-trifluoromethylpyrrolo[1,2-a]-imidazole,
2,3,7-tricyano-6-tert-butylpyrrolo[1,2-a]imidazole,
2,3,7-tricyano-6-phenylpyrrolo[1,2-a]imidazole,
2,3,7-tricyano-6-ethoxycarbonylpyrrolo[1,2-a]-imidazole,
5-chloro-2,3,7-tricyano-6-tert-butylpyrrolo[1,2-a]-imidazole,
5-chloro-2,3,7-tricyano-6phenylpyrrolo[1,2-a]-imidazole,
7-cyano-6-pethoxycarbonylpyrrolo[1,2-a]benzimidazole,
7-cyano-6-phenylpyrrolo[1,2-a]benzimidazole,
7-amido-6-ethoxycarbonylpyrrolo[1,2-a]benzimidazole,
and their addition salts with an acid.

As examples of compounds of formula (IIg), particular mention may be made of those for which:
$R_1$ is hydrogen or chlorine;
$R_2$ is cyano;
$R_3$ is methoxycarbonyl; or ethyloxycarbonyl; and
$R_5$ is cyano.

Among the compounds of formula (IIg) above, very particular mention may be made of:
5,6,8-tricyanopyrrolo[1,2-c]-1,2,3-triazole,
5,8-dicyano-6-ethoxycarbonylpyrrolo[1,2-c]-1,2,3-triazole,
4-chloro-5,8-dicyano-6-ethoxycarbonylpyrrolo[1,2-c]-1,2,3-triazole,
and their addition salts with an acid.

The acid addition salts of the compounds of the invention can be selected in particular from hydrochlorides, hydrobromides, tartrates, tosylates, benzenesulphonates, sulphates, lactates and acetates.

The compounds of the present invention, their synthesis intermediates and the processes for their preparation are described in the patents and patent applications U.S. Pat. No. 5,256,526, EP-A-557 851, EP-A-578 248, EP-A-518 238, EP-A-456 226, EP-A-488 909, EP-A-488 248 and in the following publications:

D. R. Liljegren, Ber. 1964, 3436;
E. J. Browne, J.C.S., 1962, 5149;
P. Magnus, J.A.C.S., 1990, 112, 2465;
P. Magnus, J.A.C.S., 1987, 109, 2711;
Angew. Chem. 1960, 72, 956;
and Rec. Trav. Chim. 1961, 80, 1075.

The compound or compounds of formula (I) or (II) make up preferably between 0.0005 and 12% by weight, approximately, of the total weight of the dyeing composition and, more particularly, between 0.005 and 6% by weight.

The nature of the oxidation base or bases which can be employed in the dyeing composition according to the invention is not critical. This or these oxidation base or bases are preferably selected from para-phenylenediamines, bisphenylalkylenediamines, para-aminophenols, ortho-aminophenols, heterocyclic bases, and their addition salts with an acid.

Among the para-phenylenediamines which can be employed as oxidation bases in the dyeing composition according to the invention, particular mention may be made of the compounds corresponding to the following formula (III) and their addition salts with an acid:

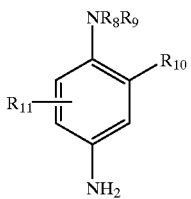

(III)

in which:
$R_8$ is a hydrogen atom or a $C_1$–$C_4$ alkyl, $C_1$–$C_4$ monohydroxyalkyl, $C_2$–$C_4$ polyhydroxyalkyl or $C_1$–$C_4$-alkoxy-$C_1$–$C_4$-alkyl radical,
$R_9$ is a hydrogen atom or a $C_1$–$C_4$ alkyl, $C_1$–$C_4$ monohydroxyalkyl or $C_2$–$C_4$ polyhydroxyalkyl radical,
$R_{10}$ is a hydrogen atom, a halogen atom, such as a chlorine atom, or a $C_1$–$C_4$ alkyl, sulpho, carboxyl, $C_1$–$C_4$ monohydroxyalkyl or $C_1$–$C_4$ hydroxyalkoxy radical, and
$R_{11}$ is a hydrogen atom or a $C_1$–$C_4$ alkyl radical.

In the formula (III) above, and when $R_{10}$ is other than a hydrogen atom, $R_8$ and $R_9$ are preferably a hydrogen atom and $R_{10}$ is preferably the same as $R_{11}$, and, when $R_{10}$ is a halogen atom, $R_8$, $R_9$ and $R_{10}$ are preferably a hydrogen atom.

Among the para-phenylenediamines of the formula (III) above, more particular mention may be made of para-phenylenediamine, para-tolylenediamine, 2-isopropyl-para-phenylenediamine, 2-β-hydroxyethylparaphenylenediamine, 2-β-hydroxyethyloxy-paraphenylenediamine, 2,6-dimethyl-paraphenylenediamine, 2,6-diethyl-para-phenylenediamine, 2,3-dimethyl-para-phenylenediamine, N,N-bis(β-hydroxyethyl)-paraphenylenediamine, 4-amino-1-(β-methoxyethyl)amino-benzene and 2-chloro-paraphenylenediamine, and their addition salts with an acid.

Among the bisphenylalkylenediamines which can be employed as oxidation bases in the dyeing composition according to the invention, particular mention may be made of the compounds corresponding to the following formula (IV) and their addition salts with an acid:

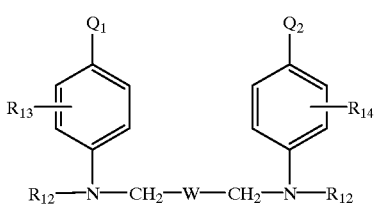

(IV)

in which:
$Q_1$ and $Q_2$ are identical or different and are a hydroxyl radical or a radical $NHR_{15}$ in which $R_{15}$ is a hydrogen atom or a $C_1$–$C_4$ alkyl radical,
$R_{12}$ is a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical whose amino moiety may be substituted,
$R_{13}$ and $R_{14}$ are identical or different and are a hydrogen or halogen atom or a $C_1$–$C_4$ alkyl radical,
W is a radical taken from the group consisting of the following radicals:

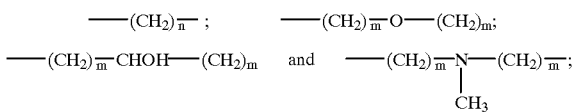

in which n is an integer from 0 to 8 inclusive and m is an integer from 0 to 4 inclusive.

Among the bisphenylalkylenediamines of formula (IV) above, more particular mention may be made of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N, N'-bis(4-methylaminophenyl)tetramethylenediamine and N,N'-bis(ethyl)-N,N'-bis(4'-amino-3'-methylphenyl)ethylenediamine, and their addition salts with an acid.

Among these bisphenylalkylenediamines of formula (IV), N,N'-bis(β-hydroxyethyl)-N,N'-bis-(4'-aminophenyl)-1,3-diaminopropanol, or one of its addition salts with an acid, are particularly preferred.

Among the para-aminophenols which can be employed as oxidation bases in the dyeing composition according to the invention, particular mention may be made of the compounds corresponding to the following formula (V) and their addition salts with an acid:

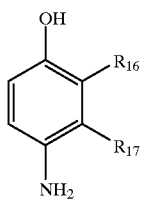

(V)

in which:
$R_{16}$ is a hydrogen atom or a $C_1$–$C_4$ alkyl, $C_1$–$C_4$ monohydroxyalkyl, $C_1$–$C_4$-alkoxy-$C_1$–$C_4$-alkyl or $C_1$–$C_4$ aminoalkyl radical, and
$R_{17}$ is a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $C_1$–$C_4$-alkoxy-$C_1$–$C_4$-alkyl radical, it being understood that at least one of the radicals $R_{16}$ and $R_{17}$ is a hydrogen atom.

Among the para-aminophenols of formula (V) above, more particular mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and their addition salts with an acid.

Among the ortho-aminophenols which can be employed as oxidation bases in the dyeing composition according to the invention, particular mention may be made of 2-aminophenol, 2-amino-1-hydroxy-5-methylbenzene, 2-amino-1-hydroxy-6-methylbenzene, and 5-acetamido-2-aminophenol, and their addition salts with an acid.

Among the heterocyclic bases which can be employed as oxidation bases in the dyeing composition according to the invention, particular mention may be made of pyridine derivatives, pyrimidine derivatives, and pyrazole derivatives, and their addition salts with an acid.

Among pyridine derivatives more particular mention may be made of the compounds described, for example, in the patents GB 1 026 978 and GB 1 153 196, such as 2,5-diaminopyridine, and their addition salts with an acid.

Among pyrimidine derivatives more particular mention may be made of the compounds described, for example, in the German patent DE 2 359 399 or Japanese patents JP 88-571 and JP 91-333 495, such as 2,4,5,6-tetraaminopyrimidine and 4-hydroxy-2,5,6-triaminopyrimidine, and their addition salts with an acid.

Among pyrazole derivatives more particular mention may be made of the compounds described in the patents DE 3 843 892 and DE 4 133 957 and patent applications WO 94/08969 and WO 94/08970, such as 4,5-diamino-1-methylpyrazole, 3,4-diaminopyrazole and 1-(4'-chlorobenzyl)-4,5-diaminopyrazole, and their addition salts with an acid.

According to the invention, the oxidation base or bases make up preferably from 0.0005 to 12% by weight, approximately, of the total weight of the dyeing composition, and more preferably still from 0.005 to 6% by weight, approximately, of this weight.

The dyeing composition according to the invention may also include one or more additional couplers other than the compounds of formula (I) and/or one or more direct dyes, so as to vary or enrich in glints the shades obtained with the oxidation bases.

The additional couplers which can be employed in the composition according to the invention may be selected from the couplers employed conventionally in oxidation dyeing, among which particular mention may be made of meta-phenylenediamines, meta-aminophenols, meta-diphenols and heterocyclic couplers such as, for example, indole derivatives and indoline derivatives, and their addition salts with an acid.

These couplers may be selected in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole and 6-hydroxyindoline, and their addition salts with an acid.

When present, these additional couplers make up preferably from 0.0005 to 5% by weight, approximately, of the total weight of the dyeing composition, and more preferably still from 0.005 to 3% by weight, approximately, of this weight.

The acid addition salts of the oxidation base or bases and/or of the additional couplers which can be employed in the dyeing composition of the invention are selected in particular from hydrochlorides, hydrobromides, sulphates and tartrates, lactates and acetates.

The medium appropriate for dyeing (or vehicle) consists generally of water or of a mixture of water and at least one organic solvent for solubilizing the compounds which would not be sufficiently soluble in water. As organic solvent mention may be made, for example, of $C_1$–$C_4$ lower alkanols, such as ethanol and isopropanol; glycerol; glycols and glycol ethers, such as 2-butoxyethanol, propylene glycol, propylene glycol monomethyl ether, diethylene glycol monoethyl ether and monomethyl ether, and aromatic alcohols, such as benzyl alcohol or phenoxyethanol, similar products, and mixtures thereof.

The solvents can be present in proportions of preferably between 1 and 40% by weight, approximately, relative to the total weight of the dyeing composition, and more preferably still between 5 and 30% by weight, approximately.

The pH of the dyeing composition according to the invention is generally between 3 and 12. It can be adjusted to the desired value using acidifying or basifying agents commonly employed in dyeing keratinous fibres.

Among the acidifying agents mention may be made, by way of example, of mineral or organic acids, such as hydrochloric acid, orthophosphoric acid, carboxylic acids, such as tartaric acid, citric acid and lactic acid, and sulphonic acids.

Among the basifying agents mention may be made, by way of example, of aqueous ammonia, alkali metal carbonates, alkanolamines such as mono-, di- and triethanolamines, and derivatives thereof, sodium hydroxide or potassium hydroxide, and the compounds of the following formula (VI):

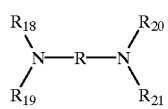

(VI)

in which R is a propylene radical which is optionally substituted by a hydroxyl group or a $C_1-C_4$ alkyl radical; $R_{18}$, $R_{19}$, $R_{20}$ and $R_{21}$ are identical or different and are a hydrogen atom or a $C_1-C_4$ alkyl or $C_1-C_4$ hydroxyalkyl radical.

The dyeing composition according to the invention may also include various adjuvants conventionally employed in hair dye compositions, such as anionic, cationic, nonionic, amphoteric and zwitterionic surfactants or mixtures thereof, anionic, cationic, nonionic, amphoteric and zwitterionic polymers or mixtures thereof, organic or inorganic thickeners, antioxidants, penetration agents, sequestering agents, fragrances, buffers, dispersants, conditioners, such as silicones, for example, film formers, preservatives and opacifiers.

The person skilled in the art will of course take care to select the abovementioned optional complementary compound(s) such that the advantageous properties intrinsic to the dyeing composition according to the invention are not, or not substantially, impaired by the intended addition(s).

The dyeing composition according to the invention may be in various forms, such as in the form of liquids, creams or gels or any other form which is appropriate for dyeing keratinous fibres, and especially human hair.

The invention also provides for the use of the compounds of formula (I) or (II) above, as coupler, in combination with at least one oxidation base for the oxidation dyeing of keratinous fibres and, in particular, of human keratinous fibres such as hair.

The invention additionally provides a method of oxidation-dyeing keratinous fibres, and especially human keratinous fibres such as hair, employing the dyeing composition as defined above.

In accordance with this method, at least one dyeing composition as defined above is applied to the fibres, the colour being developed at an acidic, neutral or alkaline pH with the aid of an oxidizing agent which is added just at the moment when the dyeing composition is employed or which is present in an oxidizing composition which is applied simultaneously or sequentially and separately.

According to a particularly preferred embodiment of the dyeing method according to the invention, the above-described dyeing composition is mixed at the time of use with an oxidizing composition which comprises, in a medium appropriate for dyeing, at least one oxidizing agent present in a quantity which is sufficient to develop a coloration. The resulting mixture is subsequently applied to the keratinous fibres and is left to act for from 3 to 50 minutes approximately, preferably from 5 to 30 minutes approximately, after which the fibres are rinsed, shampooed, rinsed again and dried.

The oxidizing agent present in the oxidizing composition as defined above may be selected from the oxidizing agents conventionally employed for the oxidation dyeing of keratinous fibres, among which mention may be made of hydrogen peroxide, urea peroxide, alkali metal bromates, and persalts, such as perborates and persulphates. Hydrogen peroxide is particularly preferred.

The pH of the oxidizing composition comprising the oxidizing agent as defined above is such that, after it has been mixed with the dyeing composition, the pH of the resulting composition applied to the keratinous fibres varies preferably between 3 and 12 approximately and, more preferably still, between 5 and 11. It is adjusted to the desired value using acidifying or basifying agents which are commonly employed in dyeing keratinous fibres and are as defined above.

The oxidizing composition as defined above may also include various adjuvants which are conventionally employed in hair dye compositions and are as defined above.

The composition which is ultimately applied to the keratinous fibres may be in various forms, such as in the form of liquids, creams, gels or any other form appropriate for dyeing keratinous fibres and, in particular, human hair.

The invention also provides a multi-compartment dyeing device or kit, or any other multi-compartment packaging system, a first compartment of which contains the dyeing composition as defined above and a second compartment of which contains the oxidizing composition as defined above. These devices can be equipped with a means permitting the desired mixture to be delivered to the hair, such as the devices described in the patent FR-2 586 913 in the name of the Applicant.

EXAMPLES

Examples 1 and 2

Dyeing in an alkaline medium

The following dyeing compositions according to the invention were prepared (contents in grams):

| Example | 1 | 2 |
|---|---|---|
| 5-cyano-4-ethoxycarbonyl-8-methyl-pyrrolo[1,2-b]-1,2,4-triazole (coupler) | 0.654 | 0.654 |
| 4-amino-1-(β-methoxyethyl)amino-benzene (oxidation base) | 0.498 | — |
| 4,5-diamino-1,3-dimethylpyrazole (oxidation base) | — | 0.384 |
| Common dye vehicle | No. 1 | No. 1 |
| Demineralized water q.s. | 100 g | 100 g |

NB: 5-cyano-4-ethoxycarbonyl-8-methylpyrrolo[1,2-b]-1,2,4-triazole was prepared by the process described in patent application EP-A-518 238.

Common Dye Vehicle No. 1:

| | |
|---|---|
| Ethanol | 20 g |
| Aqueous ammonia containing 20% NH$_3$ | 10 g |
| Sodium metabisulphite | 0.228 g |

Sequestering agent q.s.

Each of the dyeing compositions of Examples 1 and 2 above was mixed at the time of use with an equal weight of a 20-volumes hydrogen peroxide solution (6% by weight).

Each of the resulting mixtures was applied for 30 minutes to locks of natural grey hair containing 90% white hairs, permed or otherwise, in an amount of 10 g per g of hair. After rinsing, washing with a standard shampoo and drying, the locks were dyed in the shades indicated in Table 1 below:

TABLE 1

| Example | pH of the mixture | Shade obtained on natural grey hair containing 90% white hairs | Shade obtained on permed grey hair containing 90% white hairs |
|---|---|---|---|
| 1 | 9.9 | Bottle green | Bottle green |
| 2 | 9.9 | Coppery yellow | coppery orange |

EXAMPLES 3 to 6

Dyeing in a Neutral Medium

The following dyeing compositions according to the invention were prepared (contents in grams):

| Example | 3 | 4 | 5 | 6 |
|---|---|---|---|---|
| 5-cyano-4-ethoxycarbonyl-8-methyl-pyrrolo[1,2-b]-1,2,4-triazole (coupler) | 0.654 | 0.654 | — | — |
| 5-cyano-4-phenyl-8-methylpyrrolo-[1,2-b]-1,2,4-triazole (coupler) | — | — | 0.666 | — |
| 7-amido-6-ethoxycarbonylpyrrolo-[1,2-a]benzimidazole (coupler) | — | — | — | 0.813 |
| 4-amino-1-(β-methoxyethyl)amino-benzene (oxidation base) | 0.498 | 0.498 | 0.498 | 0.498 |
| Common dye vehicle | No. 2 | No. 2 | No. 2 | No. 2 |
| Demineralized water q.s. | 100 g | 100 g | 100 g | 100 g |

NB: 5-cyano-4-phenyl-8-methylpyrrolo[1,2-b]-1,2,4-triazole was prepared by the process described in the patent U.S. Pat. No. 5,256,526 and 7-amido-6-ethoxycarbonylpyrrolo[1,2-a]benzimidazole was prepared by the process described in the patent application Eβ-A-518 238.

Comon Dye Vehicle No. 2:
Ethanol 20.0 g
K$_2$HPO$_4$/KH$_2$PO$_4$ (1.5 M/1 M) buffer 10.0 g
Sodium metabisulphite 0.228 g
Sequestering agent q.s.

Each of the dyeing compositions of Examples 3 and 6 above was mixed at the time of use with an equal weight of a 20-volumes hydrogen peroxide solution (6% by weight).

Each of the dyeing compositions of Examples 4 and 5 above was mixed at the time of use with an equal quantity by weight of a 6×10$^{-3}$ mol-% aqueous ammonium persulphate solution.

Each of the resulting mixtures was applied for 30 minutes to locks of natural grey hair containing 90% white hairs, permed or otherwise, in an amount of 10 g per g of hair. After rinsing, washing with a standard shampoo and drying, the locks were dyed in the shades indicated in Table 2 below:

TABLE 2

| Example | pH of the mixture | Shade obtained on natural grey hair containing 90% white hairs | Shade obtained on permed grey hair containing 90% white hairs |
|---|---|---|---|
| 3 | 6.8 | Green-bluish grey | Green-bluish grey |
| 4 | 6.8 | Blue-mauvish grey | Blue-mauvish grey |
| 5 | 6.8 | Mauvish blue | Mauvish blue |
| 6 | 6.8 | Blue-greenish grey | Blue-greenish grey |

What is claimed is:

1. A process for oxidation-dyeing keratin fibers comprising:
   (a) applying to the fibers an effective amount for dyeing of at least one dyeing composition;
   (b) developing color at acidic, neutral, or alkaline pH in the presence of at least one oxidizing agent which is added to the dyeing composition at the time that the dyeing composition is applied, or which is present in an oxidizing composition that is applied:
      (i) separately from the dyeing composition at the same time that the dyeing composition is applied to the fibres, or
      (ii) sequentially with the dyeing composition, wherein said at least one dyeing composition, comprises, in a medium which is suitable for dyeing:
   (a) a coupler, wherein said coupler is at least one pyrroloazole compound corresponding to formulae (I) or (II), or an acid addition salt thereof:

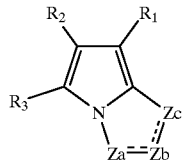

(I)

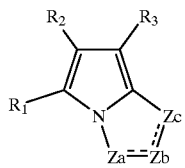

(II)

wherein:
R$_1$ is a hydrogen atom; a halogen atom; an acetylamido radical; an alkoxy radical; an aryloxy radical; an acyloxy radical; an arylthio radical; an alkylthio radical; a heteroarylthio radical; a heteroaryloxy radical; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a P-cyanophenylureido radical; an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridinyl radical;

an alkylamido; an arylamido; acetylamido; a radical $NR^{III}R^{IV}$ wherein $R^{III}$ and $R^{IV}$ each independently are a $C_1$–$C_4$ alkyl or a hydroxyalkyl; a carboxyl; or an alkoxycarbonyl radical;

$R_2$ and $R_3$ each independently are a hydrogen atom; a halogen atom; a linear or branched $C_1$–$C_5$ alkyl radical which is unsubstituted or substituted by one or two halogen, hydroxyl, alkoxy, aryloxy, amino, alkylamino, acyl or acylamino radicals; a $C_1$–$C_4$ alkoxy radical; a $C_1$–$C_4$ alkylthio radical; an arylthio radical; a benzylthio radical; an acyl radical; an acylamino radical; an acyloxy radical; a carbamoyl radical; a phenyl radical which is unsubstituted or substituted by one or two halogen, nitro, sulphonyl, $C_1$–$C_4$ alkoxy, $C_1$–$C_4$ alkyl, $C_1$–$C_3$ trifluoroalkyl, amino or alkylamino groups; an alkoxycarbonyl radical; an aryloxycarbonyl radical; a cyano radical; a nitro radical; a dialkylphosphono radical; a diarylphosphono radical; a dialkoxyphospholyl radical; a dialkylphosphinyl radical; a diarylphosphinyl radical; an alkylsulphinyl radical; an arylsulphinyl radical; an arylsulphonyl radical; an alkylsulphonyl radical; a sulphonyloxy radical; an acylthio radical; a sulphamoyl radical; a haloalkyl radical; a thiocyanate radical; or a thiocarbonyl radical;

$Z_a$, $Z_b$ and $Z_c$ each independently are a nitrogen atom or a carbon atom carrying a radical $R_4$, $R_5$, $R_6$ or $R_7$;

$R_4$ $R_6$ and $R_7$ each independently are a hydrogen atom; a linear or branched $C_1$–$C_{20}$ alkyl radical, unsubstituted or substituted by 1 or 2 radicals R, wherein R is halogen, nitro, cyano, hydroxyl, alkoxy, aryloxy amino, alkylamino, acylamino, carbamoyl, sulphonamido, sulphamoyl, trifluoromethyl, imido, alkylthio, arylthio, aryl, alkoxycarbonyl or acyl; an aryl radical, unsubstituted or substituted by 1 or 2 radicals R as defined above; or a 5- or 6-membered heterocycle having at least one nitrogen, oxygen or sulphur atom, unsubstituted or substituted by 1 or 2 radicals R as defined above;

with the proviso that when $R_4$, $R_6$ and $R_7$ are an alkyl radical, an aryl radical or a 5- or 6-membered heterocycle, said radical or said heterocycle may be attached to the carbon atom of the ring system via an oxygen, nitrogen or sulphur atom, such that $R_4$, $R_6$ and $R_7$ are $XR_4$, $XR_6$ or $XR_7$, wherein X is an oxygen, nitrogen or sulphur atom;

$R_4$, $R_6$ and $R_7$ may also each independently be a halogen atom; an acyl radical; a sulphonyl radical; a sulphinyl radical; a phosphonyl radical; a carbamoyl radical; a sulphamoyl radical; a cyano radical; a nitro radical; a siloxy radical; alkylthio; arylthio; an amino radical; an acylamino radical; arylamino; an acyloxy radical; a carbamoyloxy radical; a sulphonamide radical; an imide radical; a ureido radical; a sulphamoylamino radical; an alkoxycarbonylamino radical; an aryloxycarbonylamino radical; an alkoxycarbonyl radical; an aryloxycarbonyl radical; or a carboxyl radical;

$R_5$ is hydrogen; halogen; an acyl radical; an acyloxy radical; a carbamoyl radical; an alkoxycarbonyl radical; an aryloxycarbonyl radical; a cyano radical; a nitro radical; a dialkylphosphono radical; a diarylphosphono radical; a dialkoxyphospholyl radical; a dialkylphosphinyl radical; a diarylphosphinyl radical; an alkylsulphinyl radical; an arylsulphinyl radical; an alkylsulphonyl radical; an arylsulphonyl radical; a sulphonyloxy radical; an acylthio radical; a sulphamoyl radical; a thiocyanate radical; a thiocarbonyl radical; a haloalkyl radical; a haloaryloxy radical, a haloalkylamino radical, a haloalkylthio; an aryl optionally substituted by at least one electron-withdrawing group; or a heterocycle; and (b) at least one oxidation base or an addition salt thereof.

2. A process according to claim 1, wherein said keratin fibers are human keratin fibers.

3. A process according to claim 1, wherein said human keratin fibers are hair.

4. A process according to claim 1, wherein $R_1$ is a hydrogen atom; a $C_1$–$C_4$ alkoxy; phenoxy; phenoxy substituted by a halogen atom, a $C_1$–$C_4$ alkyl, a carboxyl group or a trifluoromethyl group; an acyloxy radical; benzyloxy; $C_1$–$C_4$ alkylthio; phenylthio; phenylthio substituted by a halogen atom, a $C_1$–$C_4$ alkyl, a carboxyl group or a trifluoromethyl group; a $C_1$–$C_4$ alkylamido; phenylamido; a radical $NR^{III}R^{IV}$, wherein $R^{III}$ and $R^{IV}$ independently are selected from a $C_1$–$C_4$ alkyl and a $C_1$–$C_4$ hydroxyalkyl; a carboxyl; or a $C_1$–$C_4$ alkoxycarboxyl radical.

5. A process according to claim 1, wherein $R_1$ is hydrogen; chlorine; bromine; methoxy; ethoxy; phenyloxy; 4-methylphenyloxy; acyloxy; benzyloxy; methylthio; ethylthio; phenylthio; 4-methylphenylthio; 2-tert-butylphenylthio; acetamido; phenylacetamido; dimethylamino; diethylamino; ethylmethylamino; or (β-hydroxyethyl)methylamino.

6. A process according to claim 5, wherein $R_1$ is hydrogen; chlorine; ethoxy; phenoxy; benzyloxy; acyloxy; acetamido; or dimethylamino.

7. A process according to claim 1, wherein $R_2$ and $R_3$ are each independently acyl; acyloxy; carbamoyl; alkoxycarbonyl; aryloxycarbonyl; cyano; nitro; alkylsulphinyl; arylsulphinyl; alkylsulphonyl; arylsulphonyl; sulphamoyl; haloalkyl; $C_1$–$C_4$ alkyl; or hydrogen.

8. A process according to claim 7, wherein $R_2$ and $R_3$ are each independently acyl; alkoxycarbonyl; nitro; cyano; arylsulphonyl; carbamoyl; haloalkyl; hydrogen; or $C_1$–$C_4$ alkyl.

9. A process according to claim 8, wherein $R_2$ and $R_3$ are each independently acetyl, ethylcarbonyl, phenylcarbonyl, methoxycarbonyl, ethoxycarbonyl, phenylsulphonyl, carbamoyl, N-ethylcarbamoyl, trifluoromethyl, methyl or ethyl.

10. A process according to claim 1, wherein:

$R_2$ is cyano, hydrogen, methyl, or phenyl; and $R_3$ is alkoxycarbonyl, aryloxycarbonyl; hydrogen; methyl; or cyano.

11. A process according to claim 10, wherein $R_3$ is methoxycarbonyl or ethoxycarbonyl.

12. A process according to claim 1, wherein $R_4$, $R_6$ and $R_7$ are each independently a linear or branched $C_1$–$C_4$ alkyl radical; aryl; phenyl substituted by a halogen, a methoxy radical, a nitro group, a cyano group, a trifluoromethyl group, or an amino group; cyano; nitro; acylamino; arylamino; alkylthio; arylthio; carbamoyl; sulphonyl; alkoxycarbonyl; aryloxycarbonyl; acyl; or hydrogen.

13. A process according to claim 12, wherein $R_4$, $R_6$ and $R_7$ are each independently hydrogen; linear or branched $C_1$–$C_4$ alkyl; aryl; or phenyl substituted by a halogen, a methoxy radical, a nitro group, a cyano group, a trifluoromethyl group, or an amino group.

14. A process according to claim 13, wherein $R_4$, $R_6$, and $R_7$ are each independently methyl, ethyl, isopropyl, or phenyl.

15. A process according to claim 1, wherein $R_5$ is acyl; alkoxycarbonyl; aryloxycarbonyl; nitro; cyano; arylsulphonyl; haloalkyl; or hydrogen.

16. A process according to claim 15, wherein $R_5$ is cyano; alkoxycarbonyl; aryloxycarbonyl; haloalkyl; or hydrogen.

17. A process according to claim 16, wherein $R_5$ is methoxycarbonyl, ethoxycarbonyl, or trifluoromenthyl.

18. A process according to claim 1, wherein said coupler is:

(i) a pyrrolo[1,2-b]-1,2,4-triazole of formula (Ia):

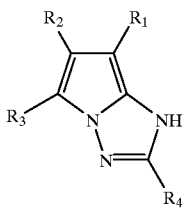

(Ia)

or (ii) a pyrrolo[2,1-c]-1,2,4-triazole of formula (Ib):

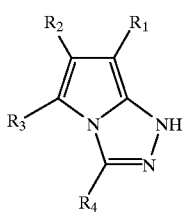

(Ib)

wherein $R_1$, $R_2$, $R_3$, and $R_4$ are as defined in claim 1; or an acid addition salt thereof.

19. A process according to claim 18, wherein said coupler is a pyrrolo[1,2-b]-1,2,4-triazole of formula (Ia), wherein:
   $R_1$ is hydrogen or chlorine;
   $R_2$ and $R_3$ are, respectively: cyano and cyano; ethoxycarbonyl and cyano; trifluoromethyl and cyano; phenylsulphonyl and cyano; trifluoromethyl and ethoxycarbonyl; ethoxycarbonyl and ethoxycarbonyl; methoxycarbonyl and methoxycarbonyl; hydrogen and hydrogen; or hydrogen and methyl; and
   $R_4$ is methyl, ethyl, isopropyl, phenyl or hydrogen.

20. A process according to claim 18, wherein said coupler is a pyrrolo[1,2-b]-1,2,4-triazole of formula (Ia), wherein:
   $R_1$ is hydrogen or chlorine;
   $R_2$ and $R_3$ are simultaneously cyano or hydrogen; and
   $R_4$ is methyl, ethyl, isopropyl, phenyl, or hydrogen.

21. A process according to claim 18, wherein said coupler is:
   3,4-dicyano-8-methylpyrrolo[1,2-b]-1,2,4-triazole,
   3,4-dicyano-8-phenylpyrrolo[1,2-b]-1,2,4-triazole,
   3,4-dicyano-8-tert-butylpyrrolo[1,2-b]-1,2,4-triazole, or
   5-Chloro-3,4-dicyano-8-methylpyrrolo[1,2-b]-1,2,4-triazole,
or an acid addition salt thereof.

22. A process according to claim 18, wherein said coupler is a pyrrolo[2,1-C]-1,2,4-triazole of formula (Ib) wherein:
   $R_1$ is hydrogen or chlorine;
   $R_2$ and $R_3$ are simultaneously cyano or hydrogen; and $R_4$ is methyl, ethyl, isopropyl, phenyl, or hydrogen.

23. A process according to claim 18, wherein coupler is:
   5,6-dicyano-3-methylpyrrolo[2,1-c]-1,2,4-triazole, or
   7-chloro-5,6-dicyano-3-methylpyrrolo[2,1-c]-1,2,4-triazole,
or an addition salt thereof.

24. A process according to claim 1, wherein said coupler is:

a) a pyrrolo[1,2-b]-1,2,4-triazole of formula (IIa):

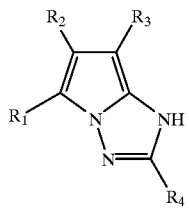

(IIa)

b) a pyrrolo[2,1-c]-1,2,4-triazole of formula (IIb):

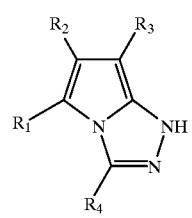

(IIb)

c) a pyrrolo[1,2-c]imidazole of formula (IIc):

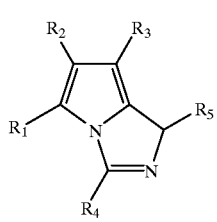

(IIc)

d) a pyrrolo[1,2-e]tetrazole of formula (IId):

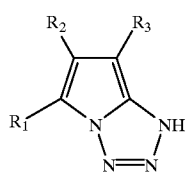

(IId)

e) a pyrrolo[1,2-a]pyrrole of formula (IIe):

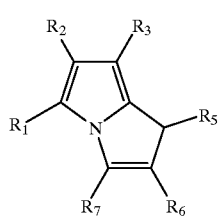

(IIe)

f) a pyrrolo[1,2-a]imidazole of formula (IIf):

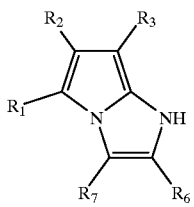

(IIf)

or g) a pyrrolo[1,2-c]-1,2,3-triazole of formula (IIg):

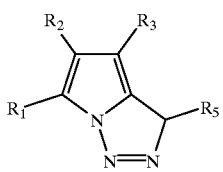

(IIg)

wherein $R_1$, $R_2$, $R_3$, $R_4$, $R_5$, $R_6$, and $R_7$ are as defined in claim 1.

25. A process according to claim 24, wherein said coupler is a pyrrolo[1,2-b]-1,2,4-triazole of formula (IIa), wherein:
   $R_1$ is hydrogen or chlorine;
   $R_2$ and $R_3$ are, respectively: methoxycarbonyl and cyano; ethoxycarbonyl and cyano; cyano and methoxycarbonyl or ethoxycarbonyl; cyano and trifluoromethyl; cyano and phenylsulphonyl; methoxycarbonyl and methoxycarbonyl; hydrogen and hydrogen; hydrogen and methyl; trifluoromethyl and cyano or trifluoromethyl and methoxycarbonyl; carboxyl and cyano; cyano and cyano; ethoxycarbonyl and ethoxycarbonyl; phenyl and cyano; or methyl and hydrogen; and
   $R_4$ is methyl, ethyl, isopropyl, phenyl or hydrogen.

26. A process according to claim 25, wherein said coupler is:
   5-cyano-4-ethoxycarbonyl-8-methylpyrrolo[1,2-b]-1,2,4-triazole,
   5-cyano-4-carboxy-8-methylpyrrolo[1,2-b]-1,2,4-triazole,
   4,5-dicyano-8-methylpyrrolo[1,2-b]-1,2,4-triazole,
   5-cyano-8-methyl-4-phenylpyrrolo[1,2-b]-1,2,4-triazole,
   4,8-dimethylpyrrolo[1,2-b]-1,2,4-triazole,
   4,5-di(ethyloxycarbonyl)-8-methylpyrrolo[1,2-b]-1,2,4-triazole,
   3-chloro-5-cyano-4-ethoxycarbonyl-8-methylpyrrolo[1,2-b]-1,2,4-triazole,
   5-cyano-4-ethoxycarbonyl-8-phenylpyrrolo[1,2-b]-1,2,4-triazole,
   5-cyano-4-carboxy-8-phenylpyrrolo[1,2b]-1,2,4-triazole,
   4,5-dicyano-8-phenylpyrrolo[1,2-b]-1,2,4-triazole,
   4,5-di(ethyloxycarbonyl)-8-phenylpyrrolo[1,2-b]-1,2,4-triazole,
   3-chloro-5-cyano-4-ethoxycarbonyl-8-phenylpyrrolo[1,2-b]-1,2,4-triazole, or
   4-cyano-5-carboxy-8-(2-nitro-5-hydroxyphenyl)pyrrolo[1,2-b]-1,2,4-triazole,
   or an acid addition salt thereof.

27. A process according to claim 24, wherein said coupler is a pyrrolo[2,1-c]-1,2,4-triazole of formula (IIb), wherein:
   $R_1$ is hydrogen or chlorine;
   $R_2$ and $R_3$ are, respectively: cyano and methoxycarbonyl; methoxycarbonyl and cyano; methoxycarbonyl and methoxycarbonyl; hydrogen and hydrogen or hydrogen and methyl; cyano and cyano; ethoxycarbonyl and ethoxycarbonyl; phenyl and cyano; or tert-butyl and cyano; and
   $R_4$ is methyl, ethyl, isopropyl, phenyl or hydrogen.

28. A process according to claim 27, wherein said coupler is:
   6,7-dicyano-3-methylpyrrolo[2,1-c]-1,2,4-triazole,
   5-chloro-6,7-dicyano-3-methylpyrrolo[2,1-c]-1,2,4-triazole,
   6,7-di(ethyloxycarbonyl)-3-methylpyrrolo[2,1-c]-1,2,4-triazole,
   7-cyano-3-methyl-6-phenylpyrrolo[2,1-c]-1,2,4-triazole, or
   7-cyano-3-methyl-6-tert-butylpyrrolo[2,1-c]-1,2,4-triazole,
   or an acid addition salt thereof.

29. A process according to claim 24, wherein said coupler is a pyrrolo[1,2-c]imidazole of formula (IIc), wherein:
   $R_1$ is acetamido, chlorine or hydrogen;
   $R_2$ and $R_3$ are, respectively, methoxycarbonyl and cyano; or cyano and cyano;
   $R_4$ is hydrogen; and
   $R_5$ is cyano.

30. A process according to claim 29, wherein said coupler is:
   6,8-dicyano-5-ethoxycarbonylpyrrolo[1,2-c]imidazole, or
   4-chloro-6,8-dicyano-5-ethoxycarbonylpyrrolo[1,2-c]imidazole,
   or an acid addition salt thereof.

31. A process according to claim 24, wherein said coupler is a pyrrolo[1,2-e]tetrazole of formula (IId):
   $R_1$ is hydrogen or chlorine; and
   $R_2$ and $R_3$ are, respectively: cyano and methoxycarbonyl; cyano and cyano; methoxycarbonyl and cyano; methoxycarbonyl and methoxycarbonyl; hydrogen and hydrogen; or hydrogen and methyl.

32. A process according to claim 31, wherein said coupler is:
   6,7-dicyanopyrrolo[1,2-e]tetrazole,
   6-cyano-7-ethoxycarbonylpyrrolo[1,2-e]tetrazole,
   5-chloro-6,7-dicyanopyrrolo[1,2-e]tetrazole, or
   an acid addition salt thereof.

33. A process according to claim 24, wherein said coupler is a pyrrolo[1,2-a]pyrrole of formula (IIe), wherein:
   $R_1$ is hydrogen or chlorine;
   $R_2$ and $R_3$ are, respectively, cyano and methoxycarbonyl;
   $R_5$ is trifluoromethyl;
   $R_6$ is phenyl or methyl; and
   $R_7$ is methyl.

34. A process according to claim 24, wherein said coupler is a pyrrolo[1,2-a]imidazole of formula (IIf), wherein:
   $R_1$ is hydrogen or chlorine; and
   $R_2$, $R_3$, $R_6$ and $R_7$ are, respectively:
   methoxycarbonyl, cyano, cyano, and phenyl;
   cyano, methoxycarbonyl, cyano, and phenyl;
   cyano, methoxycarbonyl, methoxycarbonyl, and phenyl;
   hydrogen, hydrogen, hydrogen, and hydrogen; or hydrogen, hydrogen, methyl, and methyl.

35. A process according to claim 34, wherein said coupler is:
  2,3,7-tricyano-6-methylpyrrolo[1,2-a]imidazole,
  2,3,7-tricyano-6-trifluoromethylpyrrolo[1,2-a]imidazole,
  2,3,7-tricyano-6-tert-butylpyrrolo[1,2-a]imidazole,
  2,3,7-tricyano-6-phenylpyrrolo[1,2-a]imidazole,
  2,3,7-tricyano-6-ethoxycarbonylpyrrolo[1,2-a]imidazole,
  5-chloro-2,3,7-tricyano-6-tert-butylpyrrolo[1,2-a]imidazole,
  5-chloro-2,3,7-tricyano-6-phenylpyrrolo[1,2-a]imidazole,
  7-cyano-6-ethoxycarbonylpyrrolo[1,2-a]benzimidazole,
  7-cyano-6-phenylpyrrolo[1,2-a]benzimidazole,
  7-amido-6-ethoxycarbonylpyrrolo[1,2-a]benzimidazole, or
an acid addition salt thereof.

36. A process according to claim 24, wherein said coupler is a pyrrolo[1,2-c]-1,2,3-triazole of formula (IIg), wherein:
  $R_1$ is hydrogen or chlorine;
  $R_2$ is cyano;
  $R_3$ is methoxycarbonyl or ethoxycarbonyl; and
  $R_5$ is cyano.

37. A process according to claim 36, wherein said coupler is:
  5,6,8-tricyanopyrrolo[1,2-c]-1,2,3-triazole,
  5,8-dicyano-6-ethoxycarbonylpyrrolo[1,2-c]-1,2,3-triazole, or
  4-chloro-5,8-dicyano-6-ethoxycarbonylpyrrolo[1,2-c]-1,2,3-triazole,
or an acid addition salt thereof.

38. A process according to claim 1, wherein said coupler is a hydrochloride, hydrobromide, tartrate, tosylate, benzenesulphonate, sulphate, lactate, or acetate acid addition salt.

39. A process according to claim 1, wherein said at least one pyrrolo-azole compound is present in an amount ranging from about 0.0005 to about 12% by weight relative to the total weight of said composition.

40. A process according to claim 39 wherein said at least one pyrrolo-azole compound is present in an amount ranging from about 0.005 to about 6% by weight relative to the total weight of said composition.

41. A process according to claim 1, wherein said at least one oxidation base is present in an amount ranging from about 0.0005 to about 12% by weight relative to the total weight of said composition.

42. A process according to claim 41, wherein said at least one oxidation base is present in an amount ranging from about 0.005 to about 6% by weight relative to the total weight of said composition.

43. A process according to claim 1, wherein said composition further comprises at least one additional coupler other than said at least one pyrrolo-azole compound of formula (I) or formula (II), at least one direct dye, or at least one of each.

44. A process according to claim 43, wherein said at least one additional coupler is present in an amount ranging from about 0.0005 to about 5% by weight relative to the total weight of said composition.

45. A process according to claim 44, wherein said second coupler is present in an amount ranging from about 0.005 to about 3% by weight relative to the total weight of said composition.

46. A process according to claim 1, wherein said medium suitable for dyeing comprises water or water and an organic solvent.

47. A process according to claim 46, wherein said medium suitable for dyeing comprises water and an organic solvent which is a $C_1$–$C_4$ lower alkanol, glycerol, glycol, glycol ether, an aromatic alcohol, or a mixture thereof.

48. A process according to claim 47, wherein said organic solvent is present in an amount ranging from about 1 to about 40% by weight relative to the total weight of said composition.

49. A process according to claim 48, wherein said organic solvent is present in an amount ranging from about 5 to about 30% by weight relative to the total weight of said composition.

50. A process according to claim 1, wherein said composition has a pH ranging from about 3 to about 12.

51. A process according to claim 1, wherein said composition is in the form of a liquid, cream, or gel.

52. A process according to claim 1, wherein said at least one oxidizing agent is hydrogen peroxide, urea peroxide, an alkali metal bromate, or a persalt.

53. A process according to claim 52, wherein said at least one oxidizing agent is a persalt, and further wherein said persalt is a perborate or persulphate.

54. A process according to claim 52, wherein said at least one oxidizing agent is hydrogen peroxide.

55. A process according to claim 1, further comprising mixing at the time of application and before said applying step, said at least one dyeing composition with an oxidizing composition comprising, in a medium suitable for dyeing, at least one oxidizing agent in an amount sufficient to develop coloration; and
  after said developing step, leaving said mixture on said keratin fibers for a time ranging from about 3 to about 50 minutes;
  then rinsing, washing, rinsing again and drying said keratin fibers.

56. A process according to claim 55, wherein said time ranges from about 5 to about 30 minutes.

57. A process according to claim 1, wherein the oxidation base is a hydrochloride, hydrobromide, sulphate, tartrate, lactate, or acetate acid addition salt.

58. A process according to claim 43, wherein said at least one additional coupler is a hydrochloride, hydrobromide, sulphate, tartrate, lactate, or acetate acid addition salt.

59. A process according to claim 1, wherein said at least one oxidation base is chosen from a para-phenylenediamine, a bis(phenyl)alkylenediamine, a para-aminophenol, an ortho-aminophenol, a heterocyclic base, and an acid addition salt thereof.

60. A process according to claim 59, wherein said para-phenylenediamine is a compound of formula (III) or an acid addition salt thereof:

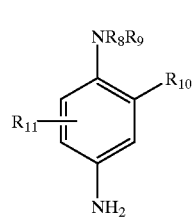

(III)

in which:
  $R_8$ is chosen from a hydrogen atom, a $C_1$–$C_4$ alkyl radical, a $C_1$–$C_4$ monohydroxyalkyl radical, a $C_2$–$C_4$ polyhydroxyalkyl radical, and a ($C_1$–$C_4$) alkoxy ($C_1$–$C_4$) alkyl radical;

$R_9$ is chosen from a hydrogen atom, a $C_1$–$C_4$ alkyl radical, a $C_1$–$C_4$ monohydroxylalkyl radical, and a $C_2$–$C_4$ polyhydroxyalkyl radical;

$R_{10}$ is chosen from a hydrogen atom, a halogen atom, a $C_1$–$C_4$ alkyl radical, a sulpho group, a carboxyl radical, a $C_1$–$C_4$ monohydroxylalkyl radical, and a $C_1$–$C_4$ hydroxyalkoxy radical; and, $R_{11}$ is chosen from a hydrogen atom and a $C_1$–$C_4$ alkyl radical.

* * * * *

UNITED STATES PATENT AND TRADEMARK OFFICE
CERTIFICATE OF CORRECTION

PATENT NO.   : 6,238,440 B1
DATED        : May 29, 2001
INVENTOR(S)  : Vidal et al.

It is certified that error appears in the above-identified patent and that said Letters Patent is hereby corrected as shown below:

Column 19, claim 21,
Line 54, change "Chloro" to -- chloro --.

Column 19, claim 22,
Line 58, change "[2,1-C]" to -- [2,1-c] --.

Column 21, claim 26,
Line 56, change "2b" to -- 2-b --.

Signed and Sealed this

Nineteenth Day of February, 2002

Attest:

JAMES E. ROGAN
*Attesting Officer*           *Director of the United States Patent and Trademark Office*